(12) United States Patent
Qi et al.

(10) Patent No.: US 11,903,999 B2
(45) Date of Patent: Feb. 20, 2024

(54) COMBINATION OF AS1411 AND SAPC-DOPS FOR THE TREATMENT OF GLIOBLASTOMA MULTIFORME

(71) Applicant: University of Cincinnati, Cincinnati, OH (US)

(72) Inventors: Xiaoyang Qi, Cincinnati, OH (US); Nikhil Shukla, Carmel, IN (US)

(73) Assignee: University of Cincinnati, Cincinnati, OH (US)

( * ) Notice: Subject to any disclaimer, the term of this patent is extended or adjusted under 35 U.S.C. 154(b) by 352 days.

(21) Appl. No.: 16/756,247

(22) PCT Filed: Oct. 15, 2018

(86) PCT No.: PCT/US2018/055836
§ 371 (c)(1),
(2) Date: Apr. 15, 2020

(87) PCT Pub. No.: WO2019/079164
PCT Pub. Date: Apr. 25, 2019

(65) Prior Publication Data
US 2020/0237866 A1    Jul. 30, 2020

Related U.S. Application Data (60) Provisional application No. 62/572,605, filed on Oct. 16, 2017.

(51) Int. Cl.
| | |
|---|---|
| *A61K 38/18* | (2006.01) |
| *A61P 35/00* | (2006.01) |
| *A61K 9/51* | (2006.01) |
| *A61K 31/685* | (2006.01) |
| *C12N 15/115* | (2010.01) |
| *A61K 9/00* | (2006.01) |

(52) U.S. Cl.
CPC .............. *A61K 38/18* (2013.01); *A61K 9/51* (2013.01); *A61K 31/685* (2013.01); *A61P 35/00* (2018.01); *C12N 15/115* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 2014/0170076 A1 | 6/2014 | Bates et al. | |
| 2015/0025029 A1* | 1/2015 | Bloembergen | A61P 35/00 530/391.1 |
| 2015/0290300 A1* | 10/2015 | Kaur | A61K 38/47 435/351 |

OTHER PUBLICATIONS

Jin et al. "Biodegradable, Multifunctional DNAzyme Nanoflowers for Enhanced Cancer Therapy," NPG Asia Materials, Mar. 24, 2017 (Mar. 24, 2017), vol. 9, No. 3, pp. 1-10.*
Victor M. Blanco et al, Phosphatidylserine-selective targeting and anticancer effects of SAPC-DOPS nanovesicles on brain tumors, Oncotarget, vol. 5, No. 16, Jul. 14, 2014, pp. 7105-7118.
Yi Jin et al, Biodegradable, Multifunctional DNAzyme Nanoflowers for Enhanced Cancer Therapy, NPG Asia Materials, 2017, (9) e365, 11 pages.
Nikhil Shukla et al, Abstract of EXTH-65. AS1411 Enhances Cytotoxicity Of SapC-DOPS Via Surface Phosphatidylserine Elevation in Glioblastoma, Nov. 6, 2017.
Extended European Search Report pertaining to corresponding European Patent Application No. 18869033.3 dated May 27, 2021.
Wojton, et al., "Systemic Delivery of SapC-DOPS Has Antiangiogenic and Antitumor Effects Against Glioblastoma", Molecular Therapy, 2013, 1517-1525, vol. 21 No. 8.
Luo, et al., "Precise glioblastoma targeting by AS1411 aptamer-functionalized poly (L-y-glutamylglutamine )-paclitaxel nanoconjugates", Journal of Colloid and Interface Science, 2017, 783-796, 490.
Cheng, et al., "AS1411-Induced Growth Inhibition of Glioma Cells by Up-Regulation of p53 and Down-Regulation of Bcl-2 and Akt1 via Nucleolin", PLOS One, pp. 1-20, Dec. 1, 2016.

* cited by examiner

*Primary Examiner* — Maury A Audet
(74) *Attorney, Agent, or Firm* — Dinsmore & Shohl LLP (57) ABSTRACT

A method of inducing cell death in a glioblastoma multiforme cancer cell is provided, the method comprising administering to the cell a combination of therapeutic agents comprising: saposin C and dioleoylphosphatidylserine (SapC-DOPS), and nucleolin aptamer AS1411, wherein cell death of the cancer cell is induced. Also provided are methods of treating glioblastoma multiforme, methods of inhibiting growth of a glioblastoma multiforme tumor, kits, and pharmaceutical compositions comprising SapC-DOPS and AS1411.

18 Claims, 8 Drawing Sheets

Specification includes a Sequence Listing.

```
SEQUENCE LISTING

<160> NUMBER OF SEQ ID NOS: 2

<210> SEQ ID NO 1
<211> LENGTH: 80
<212> TYPE: PRT
<213> ORGANISM: Homo sapiens
<220> FEATURE:
<221> NAME/KEY: MISC_FEATURE
<223> OTHER INFORMATION: Human Saposin C protein sequence

<400> SEQUENCE: 1

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
        35                  40                  45

Glu Val Val Asp Thr Tyr Gly Ser Ser Ile Leu Ser Ile Leu Leu Glu
    50                  55                  60

Glu Val Ser Pro Glu Leu Val Cys Ser Met Leu His Leu Cys Ser Gly
65                  70                  75                  80

<210> SEQ ID NO 2
<211> LENGTH: 26
<212> TYPE: DNA
<213> ORGANISM: Artificial Sequence
<220> FEATURE:
<223> OTHER INFORMATION: Synthetic guanine-rich aptamer
<220> FEATURE:
<221> NAME/KEY: misc_feature
<223> OTHER INFORMATION: Quadruplex-forming synthetic G-rich
      oligonucleotide aptamer

<400> SEQUENCE: 2
ggtggtggtg gttgtggtgg tggtgg                                        26
```

COMBINATION OF AS1411 AND SAPC-DOPS FOR THE TREATMENT OF GLIOBLASTOMA MULTIFORME

CROSS REFERENCE TO RELATED APPLICATIONS

This application is a § 371 U.S. National Stage Application of International Application No. PCT/US2018/055836 filed Oct. 15, 2018, and claims priority to U.S. Provisional Application No. 62/572,605 filed Oct. 16, 2017, the contents of which are incorporated herein by reference.

FIELD OF THE INVENTION

The present disclosure relates to methods of treating glioblastoma multiforme (GBM). Specifically, the disclosure relates to a combination therapy comprising nucleolin aptamer AS1411 and saposin C and dioleoylphosphatidylserine (SapC-DOPS) for the treatment of GBM.

BACKGROUND OF THE INVENTION

Glioblastoma multiforme (GBM) is the most common and one of the deadliest primary brain tumors. These tumors tend to be aggressive and drug resistant and patients typically have limited therapeutic options. Though there have been advances in radiation and chemotherapy in recent decades, median survival remains poor at <15 months.

SapC-DOPS (FIG. 1A), also known as BXQ-350, is a stable nanovesicle that is now undergoing study in phase 1 clinical trials. It is composed of saposin C (SapC), a lysosomal protein that catabolizes glycosphingolipids, and the phospholipid dioleoylphosphatidylserine (DOPS). It is known that SapC-DOPS selectively targets tumors in vivo by binding to surface phosphatidylserine (PS) and that higher levels of surface PS correlate with SapC-DOPS sensitivity. Previous studies have shown that SapC-DOPS successfully crosses the blood-brain barrier and can deliver magnetic resonance contrast agents to orthotopic brain tumors in mice. Wolton, et al, Systemic Delivery of SapC-DOPS Has Antiangiogenic and Antitumor Effects Against Glioblastoma, *Molecular Therapy* 21(8): 1517-25 (2013). However, compared to other tumor models, GBM models have been relatively resistant to SapC-DOPS.

AS1411 (FIG. 1B) is a 26-base pair guanine-rich oligonucleotide apatamer to nucleolin, a phosphoprotein primarily located in the nucleolus but sometimes found on the cell surface in cancer cells, that has been shown to have selective anticancer activity in a variety of tumor cell lines. AS1411 is the first aptamer to successfully progress to clinical trials. Previous studies have shown that AS1411 induces a non-apopotic mechanism of cell death known as methuosis. Anticancer effects of AS1411 have been well described in breast, lung, prostate, and renal cell cancers. Bates, et al., Discover); and Development of the G-rich Oligonucleotide AS1411 as a Novel Treatment for Cancer, *Exp. Mol. Pathol.* 86(3): 151-154 (2009). However, the anti-cancer effect of AS1411 in GBM is relatively unknown. One study has elucidated modest cytotoxic effects of AS1411 in U87-MG glioblastoma cells. This study proposes that AS1411 induces apoptosis due to increases in surface PS, an indirect marker of apoptosis, and elevations in the tumor suppressor gene p53. These results are in contrast to previously well described studies which show that AS1411 causes methuosis-induced cell death in other tumor cell lines. Moreover, U87-MG cells show relatively high levels of resistance to AS1411 when compared to non-GBM tumor cell lines ($IC_{50}$ 10 μM vs 1 μM), Cheng, et al., AS1411-Induced Growth Inhibition of Glioma Cells by Up-Regulation of p53 and Down-Regulation of Bcl-2 and Akt1 via Nucleolin, *PLoS One* 11(12) (2016).

A need exists for improved treatments for glioblastoma multiforme.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

In one embodiment, a method of inducing cell death in a glioblastoma multiforme cancer cell is provided, the method comprising administering to the cell a combination of therapeutic agents comprising: saposin C and dioleoylphosphatidylserine (SapC-DOPS); and nucleolin aptamer AS1411, wherein cell death of the cancer cell is induced.

In another embodiment, a method of treating glioblastoma multiforme cancer in a subject in need thereof is provided, the method comprising administering to the subject a combination of therapeutic agents comprising: saposin C and dioleoylphosphatidylserine (SapC-DOPS); and nucleolin aptamer AS1411.

In another embodiment, a method of inhibiting growth of a glioblastoma multiforme (GBM) tumor in a subject in need thereof is provided, the method comprising administering to the subject a combination of therapeutic agents comprising: saposin C and dioleoylphosphatidylserine (SapC-DOPS); and nucleolin aptamer AS1411, wherein growth of the tumor is inhibited.

In another embodiment, a kit for the treatment of glioblastoma multiforme (GBM) is provided, the kit comprising: a first pharmaceutical composition comprising saposin C and dioleoylphosphatidylserine (SapC-DOPS); and a second pharmaceutical composition comprising nucleolin aptamer AS1411.

In another embodiment, a pharmaceutical position is provided, the composition comprising: saposin C and dioleoylphosphatidylserine (SapC-DOPS), Wherein the SapC-DOPS is present as nanovesicles; and nucleolin aptamer AS1411, wherein the AS1411 is encapsulated. within the SapC-DOPS nanovesicles; and a pharmaceutically-acceptable excipient.

BRIEF DESCRIPTION OF THE DRAWINGS

FIG. 1. A) Structure of SapC-DOPS is illustrated; B) structure of AS1411 quadruplex dimer is illustrated.

FIG. 2. A) SapC-DOPS and AS1411 show significant, enhanced combined cytotoxic effects in U87-MG cells; 4 μM AS1411 with 40 μM SapC-DOPS. B) 4 μM AS1411 with 50 μM SapC-DOPS. Cell viability was analyzed at 96 hrs post treatment with MTT Cell Proliferation Assay. Error bars show mean +/−SD with p<0.02 by Student's t-test when comparing to control or single drug treatment arms.

FIG. 3. A) AS1411 increase surface PS in U87-MG cells without increasing PI; Cells were treated with 6 μM AS1411 for 24, 48, 72 hrs and analyzed via flow cytometry using Annexin V-FITC stain. Error bars show mean +/−SD with **p<0.02 by Student's t-test when compared to control (untreated) cells. B) Histograms showing increase in surface PS in cells treated at 72 hrs, C) Number of propidium iodide (PI) positive (dead) cells does not increase after treatment with 6 μM AS1411.

FIG. 5. A) AS1411 induces methuosis-like vacuolization in U87-MG Cells, untreated U87-MG cells; B) 1587-MG cells treated with 10 μM MIPP for 24 hrs; C) U87-MG cells treated with 15 μM AS1411 for 72 hrs. D) U87-MG cells treated with 15 μM AS1411 for 192 hrs. E) Quantification of number of cells with >5 vacuoles.

FIG. 6. A) AS1411 encapsulated in SapC-DOPS shows significant, enhanced combined cytotoxic effects in U87-MG cells; 4 μM AS1411 encapsulated in 40 μM SapC-DOPS. B) 4 μM AS1411 encapsulated in 50 μM SapC-DOPS. Error bars show mean +/−SD with p<0.02 by Student's t-test when comparing to control or single drug treatment arms.

FIG. 7. A) AS1411 encapsulated in SapC-DOPS shows significant, enhanced combined cytotoxic effects in U87-MG cells; 4 μM AS1411 encapsulated in 40 SapC-DOPS. B) 4 μM AS1411 encapsulated in 50 μM SapC-DOPS. Error bars show mean +/−SD with p<0.02 by. Student's t-test when comparing to control or single drug treatment arms.

SEQUENCE LISTING

Applicant hereby incorporates by reference a CRF sequence listing submitted herewith having a file name 10738-679_Sequence_Listing.txt created on Oct. 10, 2018.

The nucleic and amino acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. In the accompanying sequence listing:

SEQ ID NO: 1 represents a peptide sequence of saposin C.

SEQ ID NO: 2 represents a nucleic acid sequence of AS1411.

DETAILED DESCRIPTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. it will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries should be interpreted as having a meaning that is consistent with their meaning in the context of the relevant art and the present disclosure, and will not be interpreted in an idealized or overly formal sense unless expressly so defined herein.

As used herein, "glioblastoma multiforme," "GBM," and "glioblastoma" refer to grade IV primary glioma brain cancer.

As used herein a "subject" refers to a mammal. Optionally, a subject is a human or non-human primate. Optionally, a subject is a dog, cat, equine, sheep, bovine, rabbit, pig, or murine.

As used herein, the term "sequentially" refers to a treatment protocol in which administration of a first therapeutic agent is followed by administration of a second therapeutic agent.

As used herein, the term "contemporaneously" refers to administration of a first therapeutic agent and administration of a second therapeutic agent, wherein the first and second therapeutic agents are separate and are administered at substantially the same time.

The term "pharmaceutically-acceptable excipient," as used herein, means any physiologically inert, pharmacologically inactive material known to one skilled in the art, which is compatible with the physical and chemical characteristics of the particular active agent selected for use. Pharmaceutically acceptable excipients include, but are not limited to, polymers, resins, plasticizers, fillers, lubricants, diluents, binders, disintegrants, solvents, co-solvents, buffer systems, surfactants, preservatives, sweetening agents, flavoring agents, pharmaceutical grade dyes or pigments, and viscosity agents.

A "therapeutically effective amount" is defined herein in relation to the treatment of cancers as an amount that will decrease, reduce, inhibit, or otherwise abrogate the growth of a cancer cell or tumor. In some embodiments, the therapeutic agent(s) can be delivered regionally to a particular affected region or regions of the subject's body. In some embodiments, wherein such treatment is considered more suitable, the therapeutic agent(s) can be administered systemically. For example, the compound can be administered orally or parenterally. In a specific embodiment, the therapeutic agents are delivered intravenously.

The terms "treat," "treatment," and "treating," as used herein, refer to a method of alleviating or abrogating a disease, disorder, and/or symptoms thereof in a subject.

Figure 1:
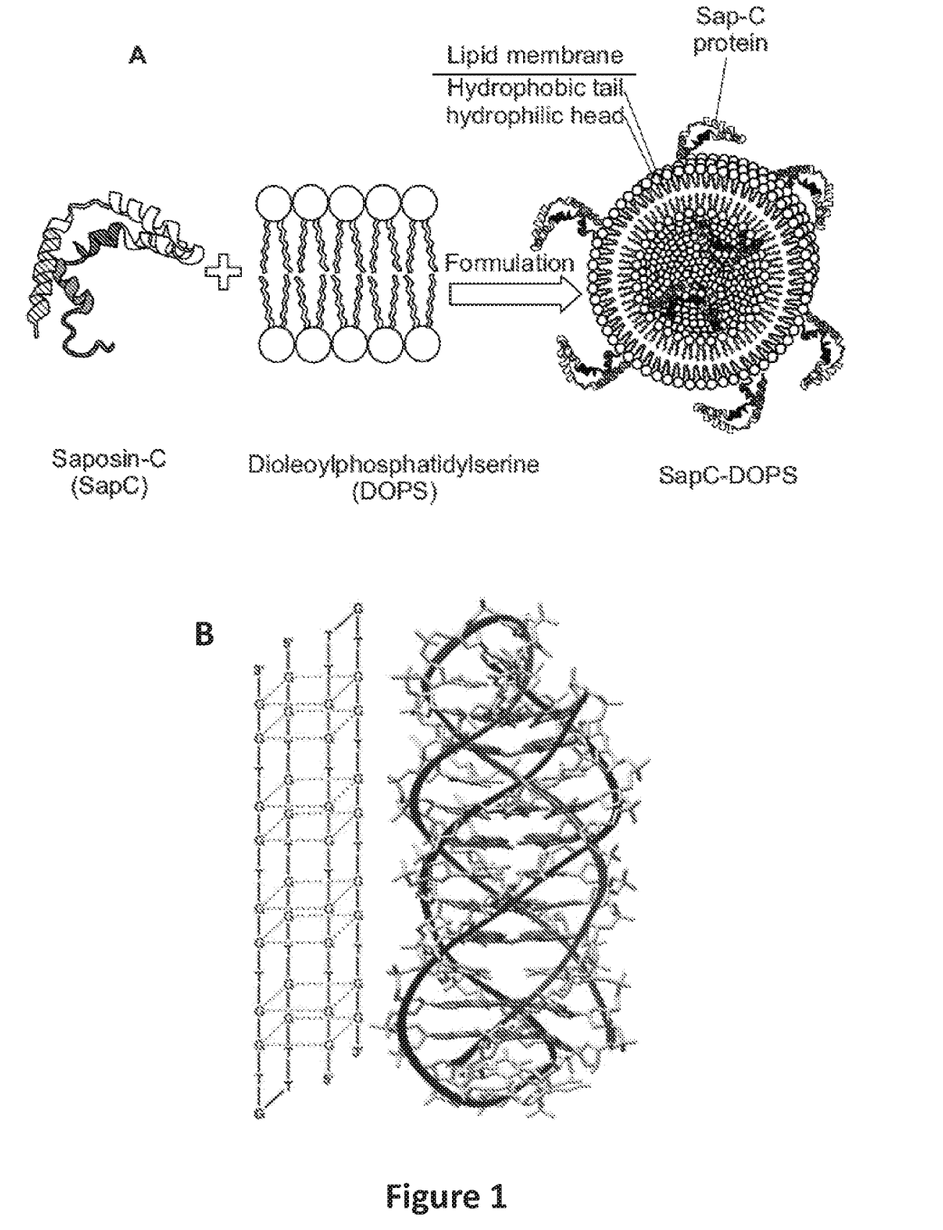

SapC-DOPS refers to a stable nanovesicle composed of saposin C (SapC), a lysosomal protein that catabolites glycosphingolipids, and the phospholipid dioleoylphosphatidylserine (DOPS) (FIG. 1A). SapC-DOPS is further described in U.S. Pat. No. 8,937,156, issued Jan. 20, 2015, which is incorporated herein by reference. In one embodiment, SapC has a protein sequence consisting of SDVYCE- VCEFLVKEVTKLIDNNKTEKEILDAFDKMCSKSL-SEECQEVVDTYGSSILSI LLEEVSPELVCSMLHLCSG (SEQ ID NO: 1). In some embodiments, SapC comprises a protein sequence having at least 75%, at least 80%, at least 85%, at least 90%, at least 95%, at least 98%, or at least 99% sequence identity to SEQ ID NO: 1.

AS1411 is a 26-base pair guanine-rich oligonucleotide apatamer to nucleolin, which is capable of forming a quadruplex structure (FIG. 1B). AS1411 is further described in WO2009/098464, published Aug. 13, 2009, which is incorporated herein by reference. In one embodiment, AS1411 has a nucleic acid sequence consisting of 5'-d (GGTGGTGGTGGTTGTGGTGGTGGTGG)-3' (SEQ ID NO: 2). In some embodiments, AS1411 comprises a nucleic acid sequence having at least 75%, at least 80%, at least 85%, at least 90%, at least 95%, at least 98%, or at least 99% sequence identity to SEQ ID NO: 2.

The present disclosure shows that co-treatment of U87-MG glioblastoma cells with AS1411 and SapC-DOPS has enhanced anti-proliferative effects when compared to either drug alone. AS1411 is demonstrated to sensitize U87-MG cells to SapC-DOPS by increasing levels of surface PS in a time dependent fashion. AS1411 is further demonstrated to induce methuosis-like morphologic changes with increased numbers of intracellular vacuoles. Interestingly, though it is known that apoptosis increases levels of surface PS, the link between methuosis and an increase in surface PS has not been previously established with clarity. The present disclosure indicates that surface PS elevation is non-specific to apoptosis-induced cell death and that surface PS may increase in other forms of cell death, including methuosis.

Compositions

The present disclosure includes compositions comprising combinations of SapC-DOPS and AS1411 and their methods of use. In certain embodiments, the AS1411 and the SapC-DOPS are formulated separately and administered as separate compositions to a cell, tumor, or subject.

In other embodiments, the SapC-DOPS nanovesicles encapsulate AS1411 oligonucleotides within the nanovesicles. Encapsulation of AS1411 within SapC-DOPS nanovesicles provides certain benefits. In some embodiments, the SapC-DOPS facilitates delivery of AS1411 across the blood brain barrier (BBB) of a subject. In some embodiments, encapsulation of AS1411 within the SapC-DOPS nanovesicles permits the administration of relatively lower doses of AS1411 and avoids toxicity issues potentially associated with high doses of AS1411.

In embodiments, pharmaceutical compositions comprising SapC-DOPS, AS1411, or SapC-DOPS encapsulating AS1411 are formulated for parenteral administration. Compositions comprising therapeutic agents described herein suitable for parenteral administration may comprise one or more pharmaceutically-acceptable excipients. Excipients include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Methods

In one embodiment, a method of inducing cell death in a glioblastoma multiforme cancer cell is provided, the method comprising administering to the cell a combination of therapeutic agents comprising: saposin C and dioleoylphosphatidylserine (SapC-DOPS); and nucleolin aptamer AS1411, wherein cell death of the cancer cell is induced. In embodiments, the SapC-DOPS is present as nanovesicles. In certain embodiments, the AS1411 and the SapC-DOPS are formulated separately and administered as separate compositions. In such embodiments, the SapC-DOPS and the AS1411 can be administered contemporaneously or sequentially. In other embodiments, the SapC-DOPS nanovesicles encapsulate AS1411 oligonucleotides within the nanovesicles. In embodiments, the AS1411 increases external cancer cell membrane surface levels of phosphatidylserine (PS), thereby enhancing the cytotoxic effect of SapC-DOPS on glioblastoma cells.

In another embodiment, a method of treating glioblastoma multiforme cancer in a subject in need thereof is provided, the method comprising administering to the subject a combination of therapeutic agents comprising: SapC-DOPS and nucleolin aptamer AS1411. In another embodiment, a method of inhibiting growth of a glioblastoma multiforme tumor in a subject in need thereof is provided, the method comprising administering to the subject a combination of therapeutic agents comprising: SapC-DOPS and AS1411, wherein growth of the tumor is inhibited. In embodiments, the SapC-DOPS is present as nanovesicles.

In certain embodiments, the AS1411 and the SapC-DOPS are formulated separately and administered as separate compositions. In such embodiments, the SapC-DOPS and the AS1411 can be administered contemporaneously or sequentially. In some embodiments, the SapC-DOPS and AS1411 are administered separately to a subject via parenteral, such as intravenous, routes.

When separately administered, SapC-DOPS is administered to a subject at a dose ranging from about 0.3 to about 1.2 mg/kg/day. In embodiments, AS1411 is administered to a subject at a dose ranging from about 20 to about 40 mg/kg/day. In an exemplary 28-day cycle, each of SapC-DOPS and AS1411 are administered daily for five days during week 1 (for example, Monday-Friday); SapC-DOPS and AS1411 are administered on alternating days for five days during week 2, beginning with SapC-DOPS (for example, SapC-DOPS is administered Monday, Wednesday, and Friday and AS1411 is administered Tuesday and Thursday). During weeks 3 and 4, SapC-DOPS and AS1411 are each administered once per week, on different days (for example, SapC-DOPS is administered Monday, and AS1411 is administered Tuesday).

In other embodiments, the SapC-DOPS nanovesicles encapsulate AS1411 oligonucleotides within the nanovesicles. When a composition comprising SapC-DOPS encapsulating AS1411 is administered, the composition is administered to a subject via a parenteral, such as intravenous, route.

A composition comprising SapC-DOPS encapsulating AS1411 is administered to a subject at a dose ranging from about 0.3 to about 1.2 mg/kg/day. In an exemplary 28-day cycle, the SapC-DOPS/AS1411 composition is administered daily for five days during week 1 (for example, Monday Friday); every other day for a total of three administrations during week 2 (for example, Monday, Wednesday, and Friday); and once per week during weeks 3 and 4 (for example, Monday only).

The skilled artisan will appreciate that the dosing schedules and amounts set forth herein are exemplary and may be varied by the attending physician in accordance with the age and physical condition of the subject to be treated, the severity of the disease, the duration of the treatment, the nature of concurrent therapy, the particular combination of therapeutic agents being employed, the particular pharmaceutically-acceptable excipients utilized, and like factors within the knowledge and expertise of the attending physician.

Kits

Provided herein are kits comprising the compositions described for the treatment of glioblastoma multiforme. In embodiments, a kit may house two containers, the first container comprising a first pharmaceutical composition comprising SapC-DOPS, and the second container comprising a second pharmaceutical composition comprising AS1411. The kits may further comprise instructions for using the components of the kit to practice the disclosed methods. The instructions for practicing the subject methods are generally recorded on a suitable recording medium. For example, the instructions may be present in the kits as a package insert or in the labeling of the container of the kit or components thereof, in other embodiments, the instructions are present as an electronic storage data file present on a suitable computer readable storage medium, such as a flash drive, CD-ROM, or diskette. In other embodiments, the actual instructions are not present in the kit, hut means for obtaining the instructions from a remote source, such as via the internet, are provided. An example of this embodiment is a kit that includes a web address where the instructions can be viewed and/or from which the instructions can be downloaded. AS with the instructions, this means for obtaining the instructions is recorded on a suitable substrate.

Specific processes, compositions and kits as described herein are illustrated in the following examples. These examples are provided for illustrative purposes and are not considered limitations on the scope of inventions.

EXAMPLES

Example 1

Determination of Cytotoxic Effects of AS1411 and SapC-DOPS

U87-MG cells were seeded onto standard 96-well cell culture plates at a confluency of 1500 cells/well. After 24 hrs, cells were treated with 4 µM AS1411 and either 40 µM or 50 µM SapC-DOPS in standard DMEM with 10% MS and penicillin/streptomycin. After 96 hrs, 10 µL of the MTT reagent was added to each well, then 4 hrs later, 100 µL of detergent were added to each well. After 24 hours of lysis, absorbance was measured at 570 nm using a microtiter plate reader.

Figure 2:
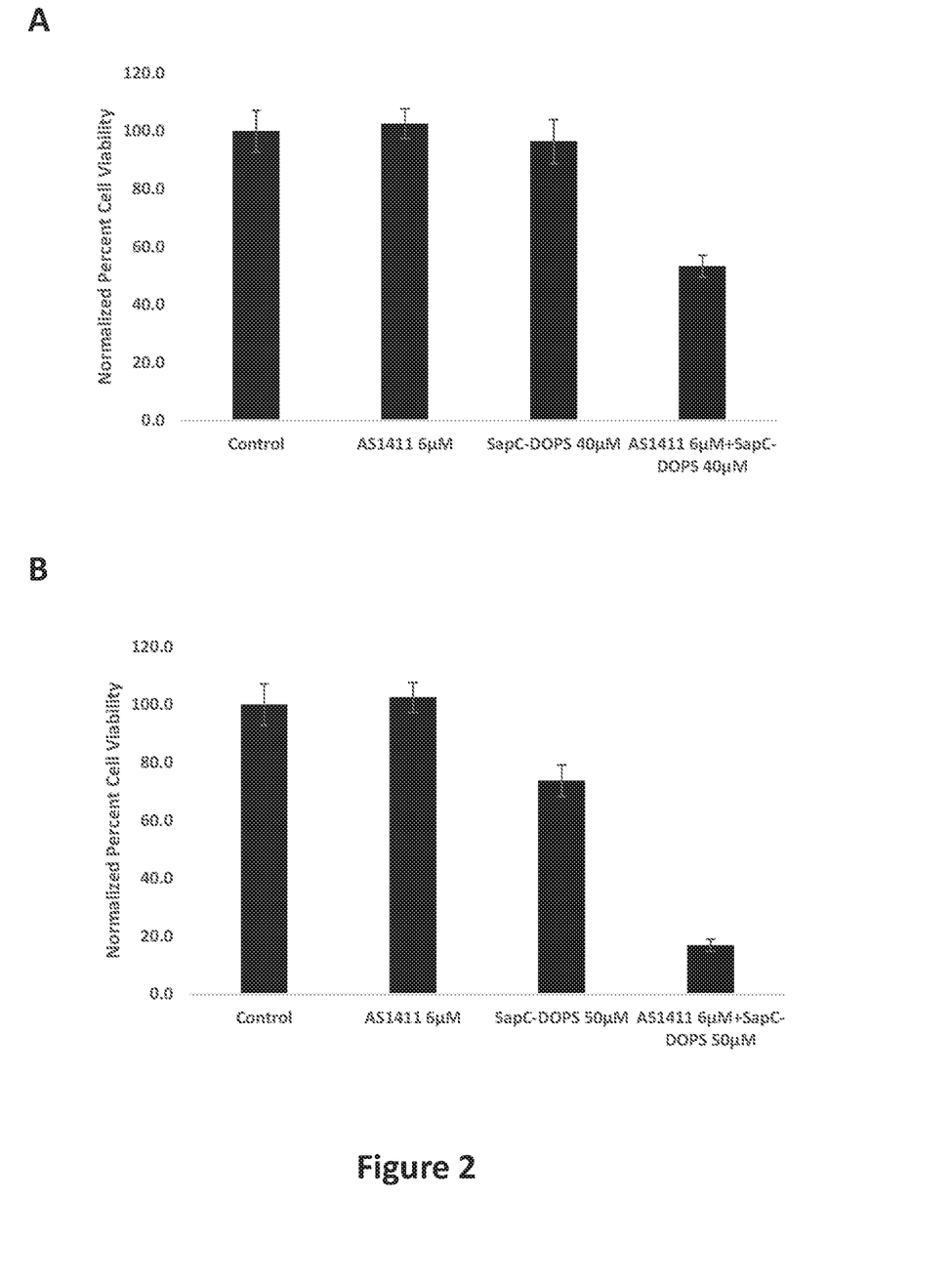

Results show SapC-DOPS and AS1411 show significant combined cytotoxic effects in 1:187-MG glioblastoma cells (FIGS. 2A and 2B).

Example 2

Determination of Cell Surface PS

U87-MG cells were seeded onto standard 60 mm cell culture dishes at ~50% confluency. After 24 hrs, 6 µM of AS1411 in DMEM was added to each dish at 24, 48, and 72 hour time points. Cells were then stained with Annexin V-FITC using a standard staining protocol and evaluated for surface PS levels using flow cytometry.

Figure 3:
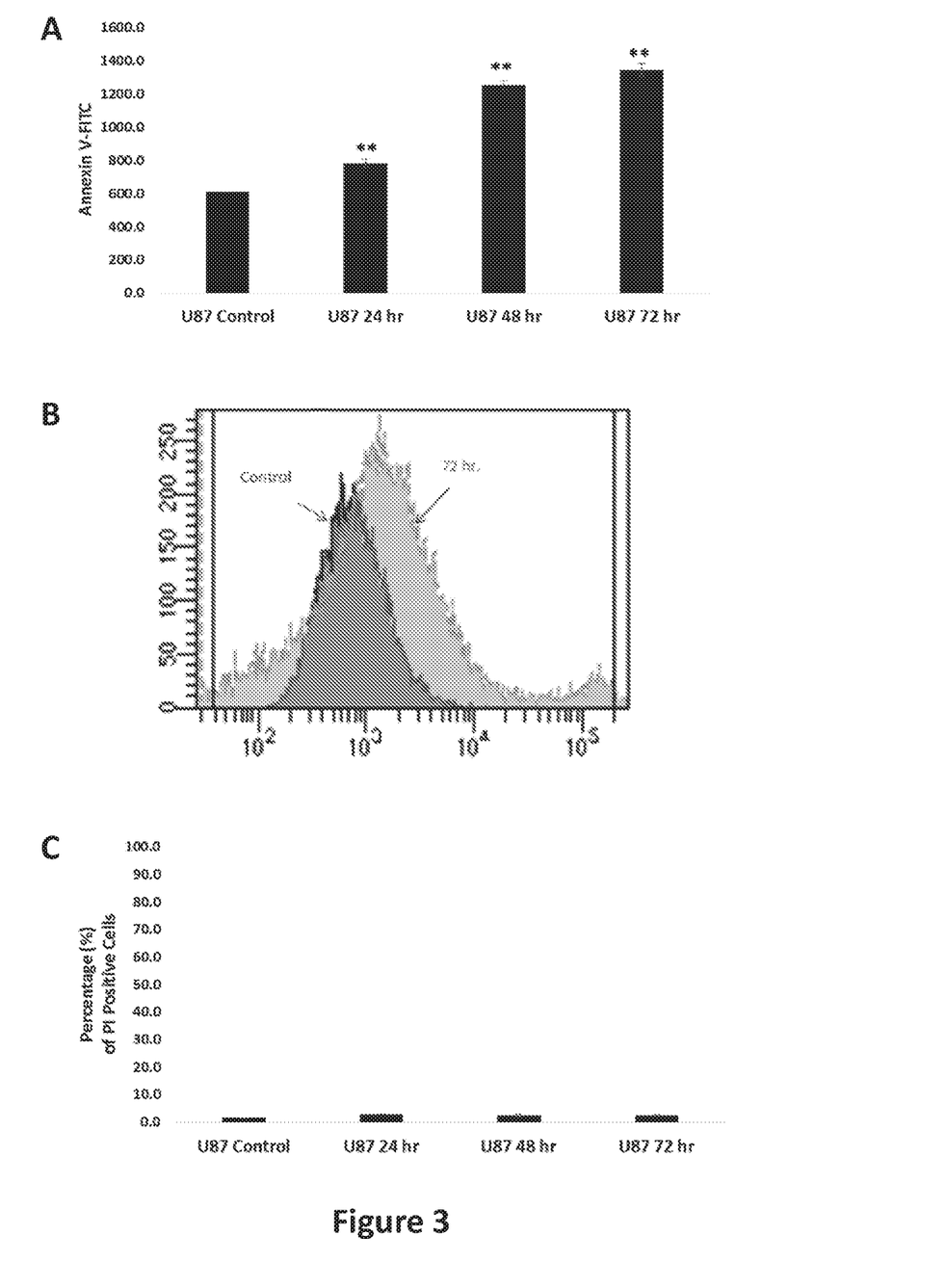

Results show AS1411 increases surface PS in U87-MG cells without increasing PI (FIGS. 3A, 3C). Histograms show increase in surface PS in cells treated at 72 hrs (FIG. 3B).

Example 3

Determination of Caspase-3 Levels as a Measure of Apoptosis

U87-MG cells were seeded onto standard 60 mm cell culture dishes at 50% confluency. After 24 hrs, 15 µM of AS1411 in DMEM and 100 µM of temozolomide (TMZ) in DMEM were added to each dish. Cells were harvested at 72 hrs and 48 hrs respectively and analyzed using the Enz-Check Caspase-3 Assay Kit from Molecular Probes utilizing the Z-DEVD-AMC substrate (incubated for 30 minutes). Fluorescence excitation/emission: 340/440 nm) was measured with a standard fluorometer.

Figure 4:
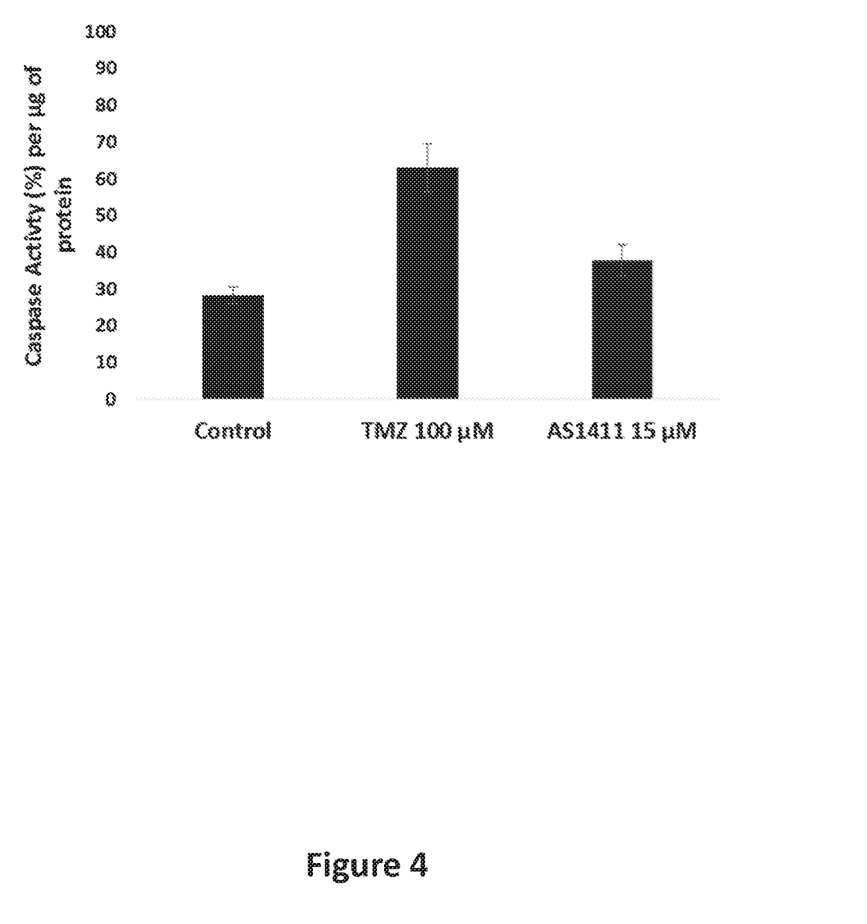
FIG. 4. shows AS1411 does not increase caspase activity as much as apoptotic drug temozolomide (TMZ), U87-MG cells were treated with 100 μM TMZ for 48 hrs and 15 μM AS1411 for 72 hrs. Caspase activity was measured with a Caspase-3 Elisa Kit. Caspase levels were normalized to total cellular protein with BCA protein assay. Error bars show mean +/−SD. Results indicate that apoptosis is not the primary cell death pathway triggered by AS1411.
Figure 5:
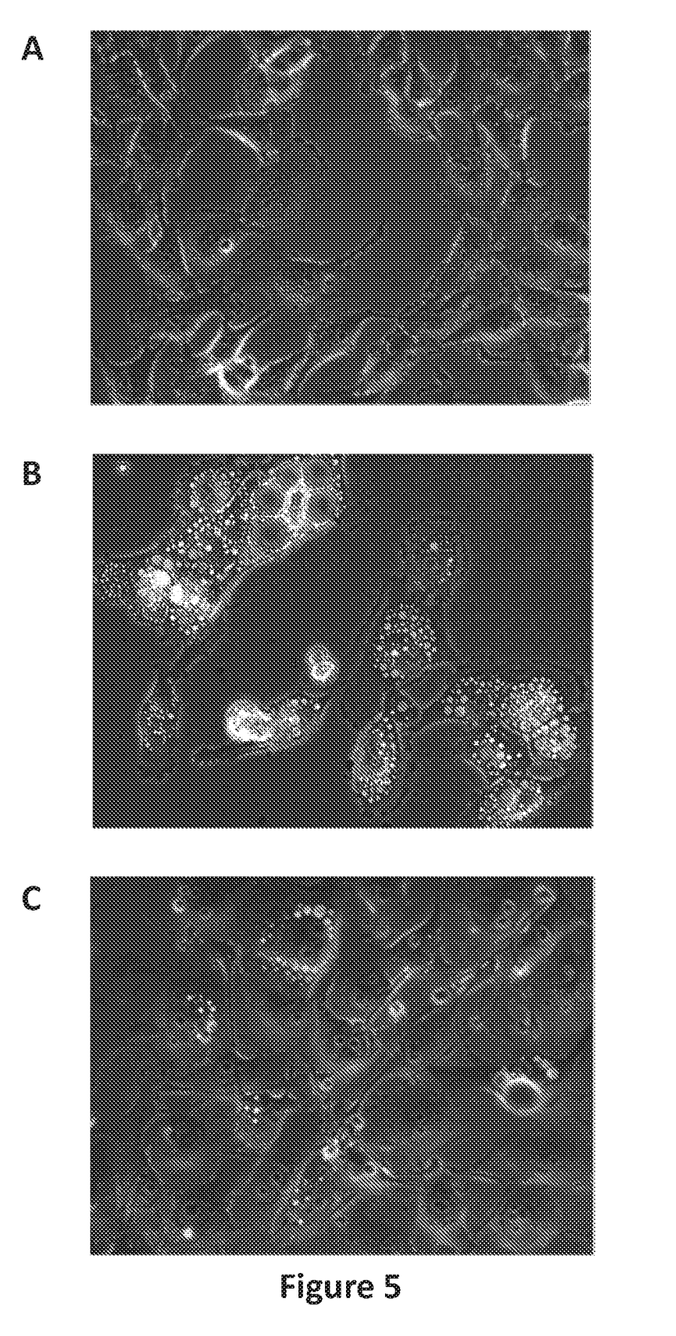

Results (FIG. 4) show that AS1411 does not increase caspase activity as much as the apoptotic drug TMZ. Results further suggest that apoptosis is not the primary cell death pathway triggered by AS1411.

Example 4

AS1411 Induces Methuosis-like Vacuolization in U87-MG Cells

U87-MG cells were grown to approximately 50% confluency in standard flat bottom 6 well cell culture plates. The cells were then treated with either 10 µM MIPP (a compound previously shown to induce methuosis) or 15 µM AS1411 for 72 hrs. Photos were taken comparing the two treatment wells with untreated control cells, using a microscope with camera.

Results show AS1411 induces morphologic changes including vacuolization in U87-MG cells which is consistent with previously described effects of AS1411 in other tumor cell lines (FIGS. 5A-5E).

Example 5

Encapsulation of AS1411 in SapC-DOPS

Lyophilized SapC-DOPS was made at a ratio of 3.6 mg SapC to 2.3 mg DOPS. Lyophilized AS1411 was obtained from Integrated DNA technology and resuspended in nuclease free water to a stock concentration of 1 nM, This stock concentration was diluted into a volume of 4 mL 0.9% NaCl to a final concentration of 4 µM AS1411. The total 4 mL of 4 µM AS1411 in normal saline was then used to resuspend lyophilized SapC-DOPS. The AS1411-SapC-DOPS suspension was sonicated in a bath sonicator at 4° C. for 30 mins. The suspension was then ultracentrifuged at 100,000 g for 30 mins at 4° C. The supernatant was carefully removed and its absorbance was measured to ensure that there was no residual AS1411 present in solution. The pellet was resuspended in 4 mL DMEM to make a final stock concentration of 100 µM SapC-DOPS with encapsulated AS1411. This stock solution was then diluted to the final concentrations of 40 µM or 50 µM SapC-DOPS used in the MTT experiments.

Example 6

Determination of Cytotoxic Effects of AS1411 Encapsulated in SapC-DOPS

U87-MG cells were seeded onto standard 96-well cell culture plates at a confluency of 1500 cells/well. After 24 hrs, cells were treated with various concentrations of AS1411, SapC-DOPS, and SapC-DOPS encapsulating AS1411 in standard DMEM with 10% FBS and penicillin/streptomycin. After 96 hrs, 10 µL of the MTT reagent was added to each well, then 4 hrs later, 100 µL. of detergent were added to each well. After 2.4 hours of lysis, absorbance was measured at 570 nm using a microtiter plate reader.

Figure 6:
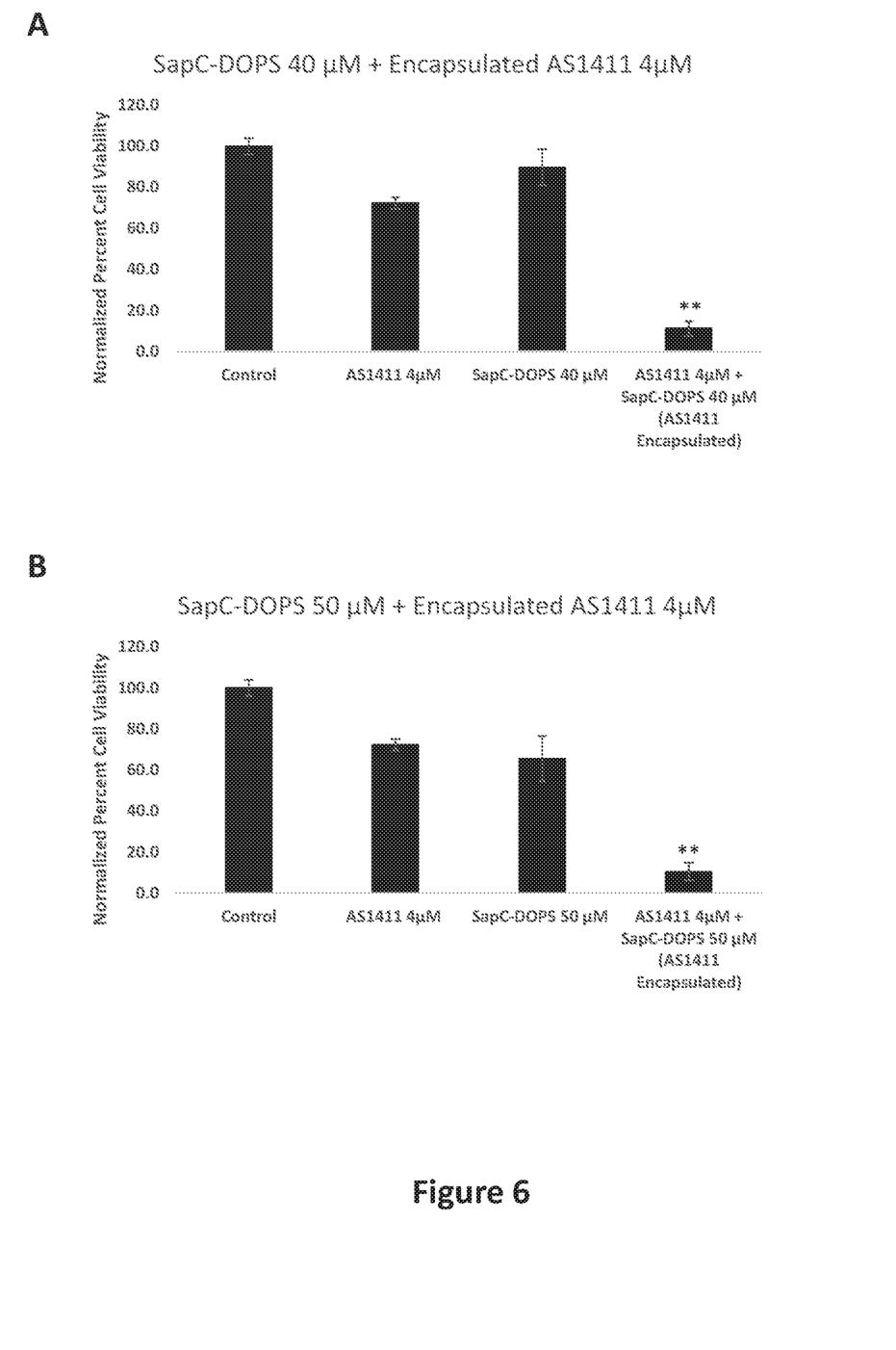
Figure 7:
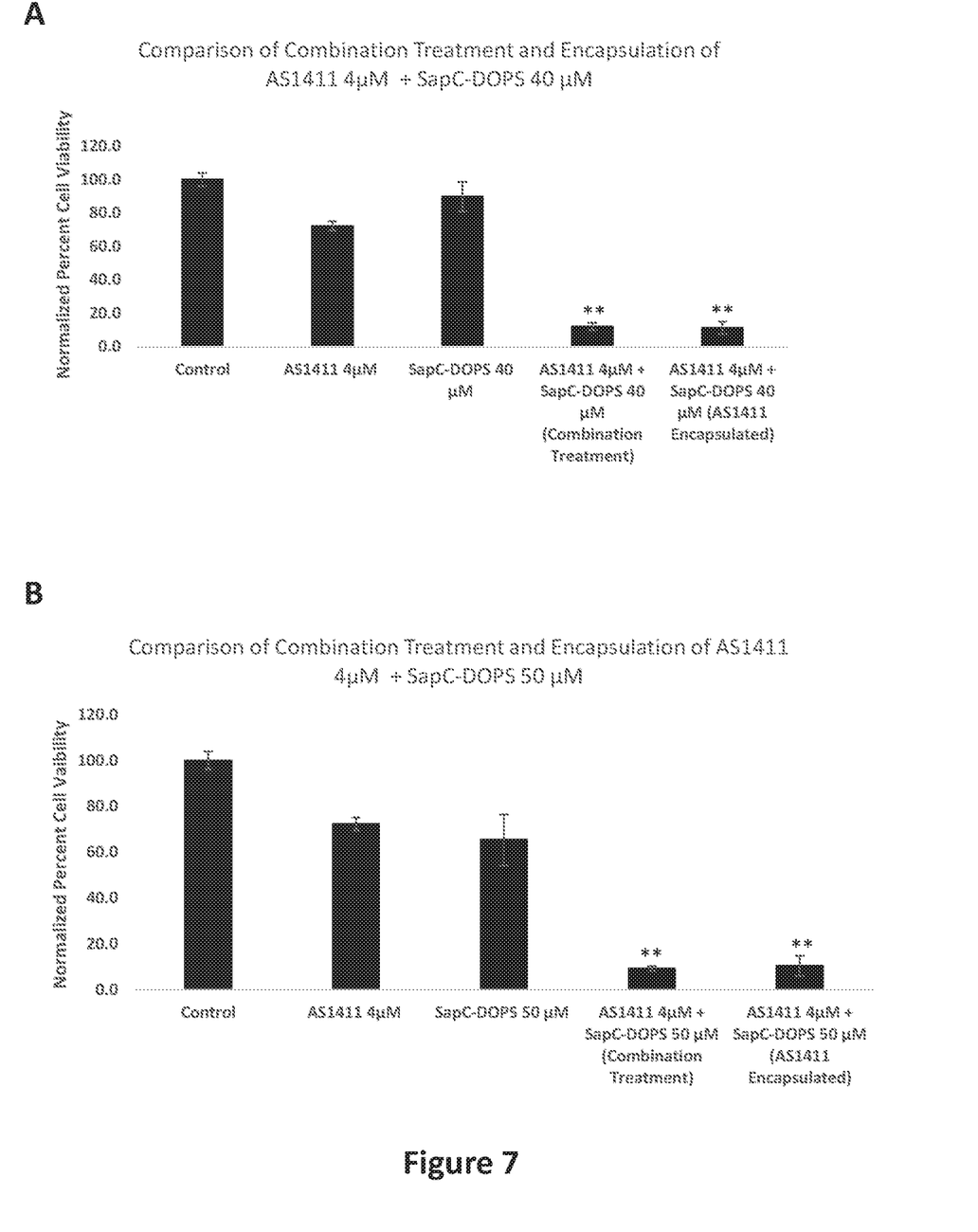

Results show 40 µM SapC-DOPS (FIG. 6A) or 50 µSapC-DOPS (FIG. 6B) encapsulating 4 µM AS1411 shows significant combined cytotoxic effects in U87-MG glioblastoma cells Additionally, results show that either combination treatment with AS1411 and SapC-DOPS or encapsulation of AS1411 in SapC-DOPS have similar cytotoxic effects (FIGS. 7A and 7B).

Patents, applications, and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

What is claimed is:

1. A pharmaceutical composition consisting of:

40-50 µM saposin C and dioleoylphosphatidylserine (SapC-DOPS), wherein the SapC-DOPS is present as nanovesicles;

4 µM nucleolin aptamer AS1411, wherein the AS1411 is encapsulated within the SapC-DOPS nanovesicles; and a pharmaceutically-acceptable excipient.

2. The pharmaceutical composition of claim 1, wherein the composition is formulated for intravenous administration.

3. A method of inducing cell death in a glioblastoma multiforme cancer cell, the method comprising administering to the cell a combination of therapeutic agents consisting of:
- 40-50 μM saposin C and dioleoylphosphatidylserine (SapC-DOPS); and
- 4 μM nucleolin aptamer AS1411,
  wherein cell death of the cancer cell is induced.

4. The method of claim 3, wherein the SapC-DOPS is present as nanovesicles.

5. The method of claim 4, wherein the AS1411 is encapsulated within the SapC-DOP S nanovesicles.

6. The method of claim 4, wherein the SapC-DOPS is administered contemporaneously or sequentially with the AS1411.

7. The method of claim 3, wherein the AS1411 increases external cancer cell membrane surface levels of phosphatidylserine.

8. A method of treating glioblastoma multiforme cancer in a subject in need thereof, the method comprising administering to the subject a combination of therapeutic agents consisting of:
- 40-50 μM saposin C and dioleoylphosphatidylserine (SapC-DOPS); and
- 4 NM nucleolin aptamer AS1411.

9. The method of claim 8, wherein the SapC-DOPS is present as nanovesicles.

10. The method of claim 9, wherein the AS1411 is encapsulated within the SapC-DOPS nanovesicles.

11. The method of claim 9, wherein the SapC-DOPS is administered contemporaneously or sequentially with the AS1411.

12. The method of claim 8, wherein administering the combination of therapeutic agents comprises an intravenous route.

13. The method of claim 8, wherein the AS1411 increases external cancer cell membrane surface levels of phosphatidylserine.

14. A method of inhibiting growth of a glioblastoma multiforme (GBM) tumor in a subject in need thereof, the method comprising administering to the subject a combination of therapeutic agents consisting of:
- 40-50 μM saposin C and dioleoylphosphatidylserine (SapC-DOPS); and
- 4 NM nucleolin aptamer AS1411,
  wherein growth of the tumor is inhibited.

15. The method of claim 14, wherein the SapC-DOPS is present as nanovesicles.

16. The method of claim 15, wherein the AS1411 is encapsulated within the SapC-DOPS nanovesicles.

17. The method of claim 15, wherein the SapC-DOPS is administered contemporaneously or sequentially with the AS1411.

18. The method of claim 14, wherein the AS1411 increases external cancer cell membrane surface levels of phosphatidylserine.

* * * * *